United States Patent [19]

Noyori et al.

[11] 4,001,249
[45] Jan. 4, 1977

[54] PROCESS FOR THE PREPARATION OF TROPANE ALKALOIDS

[75] Inventors: Ryoji Noyori, Nagoya; Yoshihiro Hayakawa, Ichinomiya; Yutaka Baba, Bisai; Shinji Makino, Hazu, all of Japan

[73] Assignee: Sanwa Kagaku Kenkyusho, Co., Ltd., Nagoya, Japan

[22] Filed: Aug. 12, 1974

[21] Appl. No.: 496,579

[30] Foreign Application Priority Data
Oct. 15, 1973 Japan ............................ 48-115424

[52] U.S. Cl. ............................. 260/292; 204/158 R
[51] Int. Cl.$^2$ ............. C07D 451/12; C07D 451/10
[58] Field of Search ................ 260/292; 204/158 R

[56] References Cited
OTHER PUBLICATIONS

Noyori et al., "J. Am. Chem. Soc." vol. 96, No. 10, May 15, 1974, pp. 3336–3338.

*Primary Examiner*—Henry R. Jiles
*Assistant Examiner*—Robert T. Bond
*Attorney, Agent, or Firm*—Hammond & Littell

[57] ABSTRACT

Process for the preparation of tropane alkaloids, more particularly of N-acyl-dehydronortropinones, dehydrotropine and tropine. The compounds can be prepared by cyclocoupling N-acyl-pyrrole with $\alpha,\alpha'$-halogenoketone in the presence of a reducing agent and, if necessary, subjecting the resulting N-acyl-dehydronortropinone to either partial reduction and then stereo-selective reduction, or stereo-selective reduction and then partial reduction.

19 Claims, No Drawings

PROCESS FOR THE PREPARATION OF TROPANE ALKALOIDS

DETAILED EXPLANATION OF THE INVENTION

The present invention relates to a process for the preparation of tropane alkaloids, more particularly to a novel process for the preparation of N-acyl-dehydronortropinones, dehydrotropine and tropine.

The compounds, more especially, dehydrotropine has a quite deep significance as a common intermediate for synthesizing the tropane alkaloids which constitute group of very important compounds in both of pharmacology and pathology.

The usability or valuableness of tropane alkaloids has been well known and various experiments or proposals have been made for synthesizing the same. Following two methods are typical for forming the basic skeleton, namely tropane skeleton.

The 1st method is to subject cycloheptadienone to the Michael reaction with methylamine, as shown in the following equation: [V. Horak and P. Zuman "Tetrahedron Lett." 746 (1961); V. Horak "Collect. Czech. Chem. Commun." 28, 1614 (1963); and A. T. Bottini and J. Gal "J. Org. Chem." 36, 1718 (1971)]

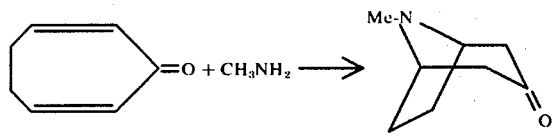

wherein Me represents methyl radical.

The 2nd method uses a Mannich reaction as shown in the following equation [R. Robinson "J. Chem. Soc." 111, 762 (1917)].

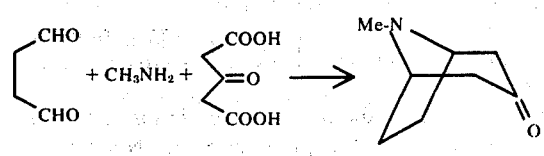

wherein Me represents methyl.

It seems to be that the methods as referred to are convenient, in view of that tropinone can be synthesized in one step, and that a relatively high yield can be attained.

Those methods, however, have disadvantages. Namely, as far the 1st one, one of the new raw materials, cycloheptadienone, is neither easily available from a market nor easily synthesized. Further, the 1st method cannot be applied for preparing tropane alkaloids other than tropinone. For the 2nd method, the synthesis of one of the raw materials, the aldehyde, is not only quite difficult, but also acetone dicarboxylic acid is too expensive. Further, the Mannich reaction can be applied only a few aldehydes. Therefore, it is impossible to apply the method for aldehyde for the purpose of synthesizing scopine.

It has been well known, as referred to, by reports made by Fordor et al that dehydrotropine, i.e. 6-tropen-3α-ol is an important compound as the intermediate for synthesizing various tropane alkaloids, as shown in the following table [G. Fordor "Progr. Phytochem." 1, P. 491 (1968); "Chemistry of the Alkaloids" S. W. Pellatier Ed., Van Nostrand Reinhold, New York, N.Y., P. 431 (1970); and "The Alkaloids" R. H. Manske Ed., Academic Press, New York, N.Y., P. 351 (1971)].

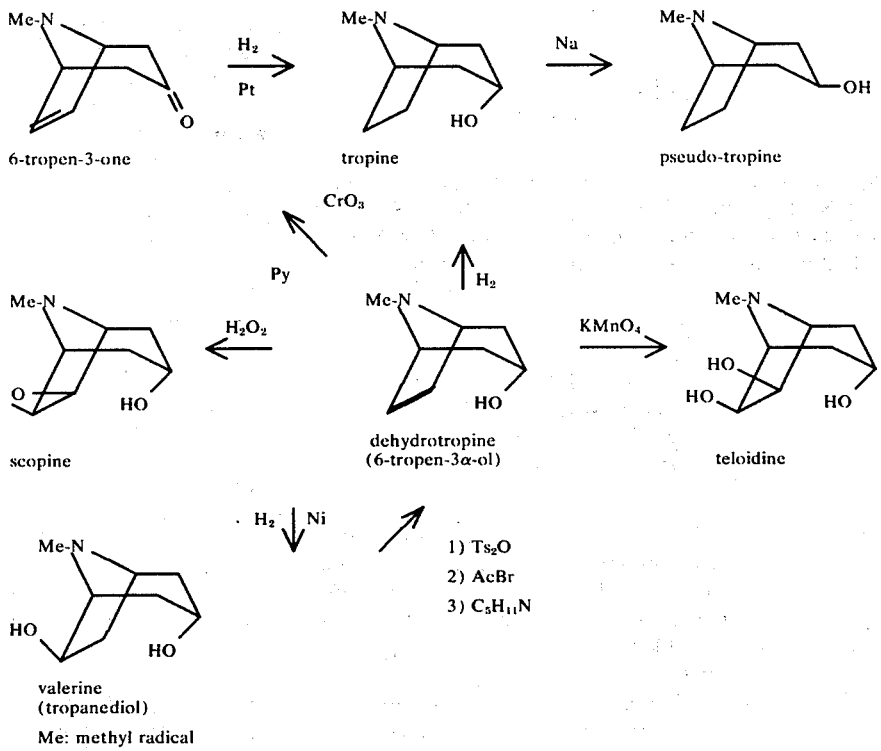

Hitherto, however, it has been known no method for effectively and advantageously synthesizing dehydrotropine and tropine.

Therefore, a principal object of the present invention is to provide a novel process for the preparation of dehydrotropine, tropine and tropanols having various substituents.

Another object of the present invention is to provide a novel process for the preparation of N-acyldehydronortropinones which are intermediate for preparing dehydrotropine, tropine and tropanols and are represented by a formula,

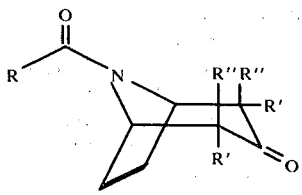

wherein R represents alkul, aryl, alkoxy or hydrogen, and R' and R" represent alkyl, hydrogen or halogen atom, respectively.

According to the present invention, the objects referred to can be attained by reacting N-acylpyrrole represented by a formula,

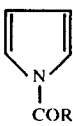

wherein R represents the meaning referred to, with α,α'-halogenoketone represented by a formula,

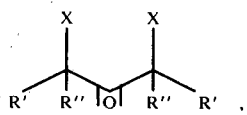

wherein R' and R" represent the meanings referred to; and X represents a halogen atom, in the presence of iron-carbonyl or zinc-copper couple, to obtain N-acyl-dehydronortropinone represented by a formula,

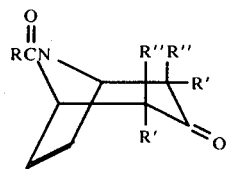

wherein R, R' and R" represent the meanings referred to, and, if necessary, either partially reducing in usual manner and then stereo-selectively reducing, or stero-selectively reducing and then partially reducing in usual manner N-acyldehydronortropinone.

It is convenient to use either tetrabromoacetone or α,α'-dibromodiethylketone, as halogenoketone employed for the present invention as one of the raw materials. As the reagent or reducing agent for the cyclocoupling reaction, ironcarbonyl is preferable, in view of yield of the product, but, it is preferable to use zinc-copper couple for the purpose of stereo-chemical selectivity. The reduction of ketocarbonyl or N-acyl radical may be carried out with use of a metal hydride. Dialkylaluminumhydride, more particularly, diisobutylaluminumhydride is most preferable to use as the metal hydride, since, if the compound is employed, simultaneous reduction of ketocarbonyl and N-acyl radicals is possible. However, it is, of course, possible to stereo-selectively reduce ketocarbonyl radical with use of $Zn(BH_4)_2$, lithiumalkoxyaluminumhydride or the like and then reduce the N-acyl radical with use of litiumaluminumhydride or the like.

Reduction between 6 and 7 positions may be carried out in a usual manner, for instance, by catalystic hydrogenation in the presence of Pd/C catalyst.

The invention will now be further explained by referring to examples. These examples are preferred embodiments of the invention and are not to be construed in limitation thereof.

EXAMPLE 1

Preparation of N-acetyl-2,4-dimethyldehydronortropinone [N-acetyl-2,4-dimethyl-8-azabicyclo(3,2,1)oct-6-en-3-one]

To a round bottom flask (30 ml), a three-way cock was mounted. To one of three branches of the cock, a ballon filled with nitrogen gas was attached, while one of the branches was communicated to a vacuum pump. After 876 mg (2.4 mmol) of $Fe_2(CO)_9$ had been charged into the flask, the vacuum pump was actuated to remove air in the sealed flask. In the flask, thereafter, nitrogen gas was introduced from the balloon. In the flask, 10 ml of benzene, 0.500 ml (521 mg, 4.79 mmol) of N-acetylpyrrole and 0.284 ml (488 mg, 200 mmol) of 2,4-dibromopentan-3-one were injectionally charged. The mixture was covered by a copper sulfate filter and reacted at room temperature by applying light beam (>350nm), while the mixture was often stirred slowly with use of a magnetic stirrer (a rotor of the stirrer was previously placed in the flask). After having reacted for 48 hours, the mixture was subjected to gas chromatography (vpc, 10% SE 30, 1.5m, 100°C, 25 ml) to know the presence of the starting material ketone. Therefore, the reaction by applying light beams was further continued for 24 hours and then 30 ml of an aqueous solution of saturated by potassium nitrate-sodium carbonate was added to the reaction mixture. The resulting solution was extracted in 8 times with use of ethyl acetate. The extracts were combined together, dried on sodium sulfate anhydride and then treated under a reduced pressure at room temperature to remove the solvent contained therein and to obtain a red oily substance. The oily substance was dissolved in 2 to 3 ml ethyl acetate and passed through a short alumina column and then evaporated to remove the solvent and to obtain 816 mg of an yellowish oily substance. According to NMR spectrum analysis, it has been confirmed that this oil consists of 2-acetyl-2,4-dimethyl-dehydronortropinone (80%) and unreacted starting materials (20%). N-acetyl-2,4-dimethyldehydronortropinone could be isolated by subjecting the oily substance to a preparative thin layer alumina chromatography [0.5 mm, 20 × 20 cm, devloped by one time with use of ethyl-benzene (1:10)], detected by a hot wire, scraping up the part of Rf 0.2 and then extracting with use of ethyl acetate (yield: 310 mg, 80%).

The compound showed the following analytical results:

IR spectrum (CCl$_4$) cm$^{-1}$: 1715, 1658, 1440, 1417.
Mass spectrum (m/e): 193 (M$^+$), 151.

EXAMPLE 2

Preparation of N-carbomethoxy-2,4-dimethyldehydronortropinone [N-carbomethoxy-2,4-dimethyl-8-azabicyclo (3,2,1)oct-6-en-3-one]

To a reaction vessel (100 ml) containing 10 g (27.5 mmol) of Fe$_2$(CO)$_9$ and a rotor for magnetic stirring, a three-way cock was mounted. To one of three branches of the cock, a balloon filled with nitrogen gas was attached, the remaining branch of the cock has connected to a vacuum pump. After removed air in the vessel by actuating the pump, nitrogen gas was introduced in the flask from the balloon. Thereafter, 80 ml of benzene, 2.25 ml (20 mmol) of N-carbomethoxypyrrole and 2.82 ml (20 mmol) of 2,4-dibromopentan-3-one were injectionally charged in the reaction vessel and then light beam was applied to the resulting mixture (using CuSO$_4$ filter, >350nm), while stirring the mixture at room temperature, to initiate the reaction. The reaction solution bubbled vigorously and the color thereof gradually changed into dark brown.

After lapsed 10 hrs., the reaction solution was analyzed by a gas chromatography (OV$_1$ 3%, 80° to 140° C) to find that ketone has almost been exhausted.

The reaction was stopped by stopping the radiation of light beam. To the reaction solution, 100 ml of ethyl acetate was added and then the resulting mixture was poured into 200 ml of potassium nitrate-sodiumbicarbonate saturated solution and extracted with use of ethyl acetate (4 times). The combined extracts were dried on sodium anhydride and concentrated under a reduced pressure to obtain 5g of a brownish oily substance.

The oily substance was carefully separated and purified with a silica-gel column and ethyl ether/n-hexane mixture (1 : 5) as the elusion agent to obtain 2.7g of following three isomers in a ratio of 1.5 : 1 : 1 (Yield 65%). IR spectrums of the isomers were 1700 to 1710 cm$^{-1}$ (C—O), respectively.

Isomer I

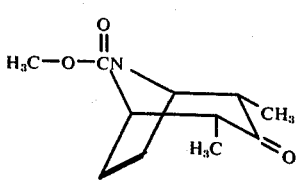

mp. 60 to 61° C
NMR spectrum (CCl$_4$) δ:
6.2 – 6.3 (m, 2H)
4.5 – 4.8 (m, 2H)
3.72 (s, 3H)
2.3 – 2.9 (m, 3H)
1.00 (d, 6H, J = 7Hz)

Isomer II

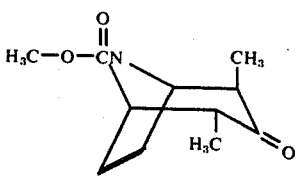

Oily substance
NMR spectrum (CCl$_4$) δ:
6.2 – 6.3 (m, 2H)
4.5 – 4.8 (m, 2H)
3.73 (s, 3H)
2.0 – 3.0 (m, 2H)

-continued 1.23 (d, 3H, J = 7Hz)
1.01 (d, 3H, J = 7Hz)

Isomer III

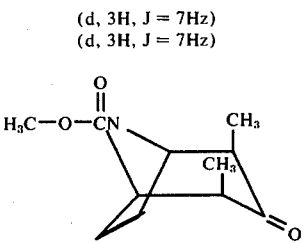

mp. 63 to 64° C.

EXAMPLE 3

Preparation of N-carbomethoxy-2,4-dibromodehydronortropinone [N-carbomethoxy-2,4-dibromo-8-azabicyclo (3,2,1)oct-6-en-3-one]

To 1.0 g (3.0 mmol) of Fe$_2$(CO)$_9$, 7.5 ml of benzene solution of tetrabromoacetone (2.5 ml/1 mmol) was added under nitrogen atmosphere and the resulting mixture was heated to 50° C. After 5 min., 0.115 ml (125 mg, 1.0 mmol) of N-carbomethoxypyrrole was added to the mixture and then the resulting mixture was stirred for 72 hrs. at said temperature. To the reaction solution, ethyl acetate (about 15 ml) was added and undissolved substances therein were filtered off. The remaining organic solution was concentrated to obtain a tar-like black oily substance. The substance was subjected to a thin layer silica gel chromatography to find three large spots (developing solvent= ethyl acetate/n-hexane 1:3 mixture; Rf= 0.66, 0.60 and 0.32). These products were subjected a preparative thin layer silica gel chromatography. One of the compounds, the compound having Rf=0.66, was obtained in a pure form but the other two compounds could only be obtained in the form of mixture. It seemed to be that the compounds are of following isomers I, II and III, listing from larger to smaller Rf values, which is monobromo compound formed by reduction of isomer I or II. Yield was 220 mg (65%) (Isomers I + II).

The isolated isomer (Isomer I) was refined by recrystallization with use of ethyl acetate/n-hexane mixture to obtain plate-like white crystals (mp. 155° – 157°C).

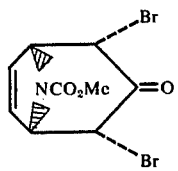 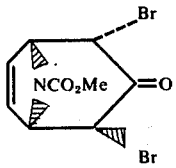

I                II

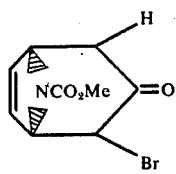

III

In the formulae, Me represents a methyl radical.

EXAMPLE 4

Preparation of N-carbomethoxy-2,4-dibromodehydronortropinone [N-carbomethoxy-2,4-dibromo-8-azabicyclo(3,2,1)oct-6-en-3-one]

A 100 ml reaction vessel, in which 1.6g (24 mmol) of Zn—Cu couple was placed and which was filled with nitrogen gas, was cooled to −5° C with use of a dry ice-methyl alcohol bath and then 20ml of dimethoxyethane and 4.6 ml (40 mmol) of N-carbomethoxypyrrole were injectionally charged in the vessel. To the mixture, thereafter, dimethoxyethane solution of tetrabromoacetone (7.5g, 210 mmol/10ml) was charged slowly over 30 min. After stirred continuously the resulting mixture for 30 min. at −5°C, the mixture was left to stand for to raise up its temperature to room one and stirred for further 1 hr. During the reaction, the reaction solution became gradually to dark brown in color. Thereafter, the reaction mixture was checked by a thin layer chromatography (silica gel, ethyl ether/n-hexane = 1 : 1) to confirm spots which coincide with those of a control or sample. The reaction was stopped and the reaction solution was concentrated under a reduced pressure. To the resulting concentrated solution, 80 ml of distilled water was added and then filtered off the forming precipitate. The resulting precipitate was washed with ethyl acetate and combined with the filtrate, and then extracted 4 times with ethyl acetate. The combined organic layer was washed with aqueous saturated solution of potassium nitrate, dried on sodium sulfate anhydride and concentrated under a reduced pressure to obtain 10 g of a dark brownish oily substance.

The oily substance was subjected to a silica gel column chromatography (ethyl acetate/n-hexane = 1 : 20 to 1 : 1) to eluviate initially about 5g of non-reacted raw material pyrrole containing impurities and then about 1.8g of the desired 1:1 adduct. The eluviated substance was refined by recrystallization to obtain 830 mg of white crystals melting at 155° to 157°C (Yield: 12%).

EXAMPLE 5 to 9

General operation regarding cyclocoupling reaction between N-acylpyrrole and $\alpha,\alpha'$-halogenoketone According to the procedures or operations described in Examples 1 to 4, a mixture consisting of a N-acyl pyrrole and $\alpha,\alpha'$-halogenoketone was stirred for about 24 hrs. at near room temperature under nitrogen atmosphere, with use of $Fe_2(CO)_9$ or Zn-Cu couple as reducing agent and benzene as solvent (It is preferable to radiate a visible ray having wave length longer than 350 nm, when an alkylsubstituted halogenoketone is used).

After completed the reaction, the reaction mixture was filtered, distilled to remove the solvent and then the resulting residue was subjected to a silica gel or alumina thin layer chromatography to isolate and refine the objective compound represented by the following formula in such yield shown in following Table 1.

Table 1

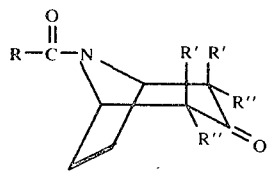

Objective compounds obtained through cyclocoupling between N-acylpyrrole and $\alpha,\alpha'$-halogenoketone, and yields and physical constants thereof

| Example No. | R | R' | R'' | Yield % | IR spectrum cm$^{-1}$ | Mass spectrum m/c (M$^+$) |
| --- | --- | --- | --- | --- | --- | --- |
| 5 | $CH_3$ | $i-C_3H_7$ | H | 63 | 1713 1660 | 249 |
| 6 | $CH_3$ | $CH_3$ | $CH_3$ | 75 | 1700 1660 | 221 |
| 7 | H | $CH_3$ | $CH_3$ | 53 | 1715 1680 | 207 |
| 8 | $C_6H_5$ | $CH_3$ | $CH_3$ | 58 | 1708 1660 | 283 |
| 9 | $OC_6H_5$ | $CH_3$ | $CH_3$ | 40 | 1705 (br) | 299 |

REFERENCIAL EXAMPLE 1

Preparation of N-acetyl-2,4-dimethylnortropinone [N-acetyl-2,4-dimethyl-8-azabicyclo(3,2,1)octan-3one]

In a 30 ml reaction vessel, 1.16g of N-acetyl-2,4-dimethyl-8-azabicyclo(3,2,1) oct-6-en-3-one prepared by the method described in Example 1, 20 ml of distilled ethyl alcohol, a rotor for magnetic stirring and 200 mg of catalyst (Pd/C) were charged and a three-way cock was mounted on the reaction vessel. To one of three branches of the cock, a balloon filled with hydrogen gas was attached, the remaining branch was connected to a vacuum pump. After removed air in the vessel by actuating the pump, hydrogen gas was introduced in the vessel from the balloon to make the spaces in the vessel hydrogen atmosphere and then the mixture accommodated in the vessel was magnetically stirred for 16 hrs. at room temperature.

Thereafter, the reaction mixture was checked by a thin layer chromatography (alumina, ethyl ether/n-hexane = 1 : 1) to find that a spot not disappeared with aqueous solution of permanganate appears at a portion showing a Rf value substantially same with that for the raw material.

The reaction mixture was filtered to remove the catalyst and then the resulting filtrate was concentrated under a reduced pressure to obtain 1g of an yellowish oily substance. This oily substance was checked by a gas chromatography ($OV_1$ 3%, 170° C) to find that no raw material presents.

NMR spectrum ($CCl_4$) δ;
4.8 – 4.0 (m, 2H, $H_1$, $H_5$)
3.0 – 2.4 (m, 2H, $H_2$, $H_4$)
2.13 (s, 3H, $COCH_3$)
2.2 – 1.3 (m, 4H, $CH_2$)
1.3 – 0.8 (m, 6H, $CHCH_3$)
(cis isomer 80.98d, J = 7.0Hz)

REFERENCIAL EXAMPLE 2

Preparation of N-carbomethoxy-2,4-dimethylnortropinone [N-carbomethoxy-2,4-dimethyl-8-azabicyclo(3,2,1)-octan-3-one]

In a 30 ml reaction vessel, 970 mg of N-carbomethoxy-2,4-dimethyl-8-azabicyclo(3,2,1)oct-6-en-3-one prepared by the method according to Example 2, 20 ml of distilled ethyl alcohol, a rotor for magnetic stirring and 200 mg of catalyst (Pd/C) were charged and a three-way cock was mounted on the vessel. To one of three branches of the cock, a balloon filled with hydrogen gas was attached and then the inside space of the vessel was made hydrogen atmosphere. The reactants in the vessel were stirred for 15 hrs. at room temperature and then the reaction mixture was checked by a gas chromatography ($OV_1$ 3%, 170° C) to confirm that no unreacted raw material presents.

The reaction mixture was filtered to remove the catalyst and then the resulting filtrate was concentrated under a reduced pressure to obtain 960 mg of an yellowish oily substance. According to NMR spectrum, the oily substance was identified as N-carbomethoxy-2,4-dimethylnortropinone.

NMR spectrum ($CCl_4$) δ:
4.5 – 4.0 (m, 2H, $H_1$, $H_5$)
3.72 and 3.68 (s, 3H, $COOCH_3$)
3.0 – 1.3 (m, 6H, $H_2$, $H_4$, > $CH_2$)
1.3 –0.8 (m, 6H, > $CHCH_3$)

REFERENCIAL EXAMPLE 3

Preparation of N-carbomethoxynortropinone [N-carbomethoxy-8-azabicyclo(3,2,1)octan-3-one]

100 mg of 10% Pd/C, 200 mg of N-carbomethoxy-2,4-dibromo-8-azabicyclo(3,2,1)oct-6-en-3-one prepared according to the method described in Example 3 or 4, and 4.0 ml of ethyl alcohol were charged in a reaction vessel and the mixture was stirred for 16 hrs. at room temperature under a hydrogen atmosphere. The reaction mixture was filtered to remove the catalyst and then the solvent in the filtrate was concentrated under a reduced pressure to obtain an yellowish oily substance. The oily substance was dissolved in about 10 mg of ethyl acetate and the resulting solution was stirred for a few minutes after added thereto $NaHCO_3$. The formed precipitate was filtered and an organic layer thereof was concentrated to obtain 115 mg of white crystals. The crystal was refined by a preparative thin layer chromatography ($SiO_2$, ethyl acetate/n-hexane = 1 : 1) to obtain 99 mg (yield 92%) of white crystalline N-carbomethoxy-8-azabicyclo(3,2,1)octan-3-one. A sample for analytical purpose was obtained by recrystallization from benzene/n-hexane mixture. m.p. 60° to 61° C.

IR spectrum ($CHCl_3$) $cm^{-1}$:
1713 (C=C), 1695 $cm^{-1}$ ($NCOOCH_3$)
NMR spectrum ($CDCl_3$) δ:
1.5 – 3.0 (m, 8H, $H_2$, $H_4$, $H_6$, $H_7$)
3.76 (s, 3H, $OCH_3$)
4.3 – 4.7 (m, 2H, $H_1$, $H_5$)
Mass spectrum (m/e):
183 ($M^+$)

REFERENCIAL EXAMPLE 4

Preparation of N-carbomethoxy-2,4-dibromonortropinone [N-carbomethoxy-2,4-dibromo-8-azabicyclo(3,2,1)octan-3-one]

200 mg of N-carbomethoxy-2,4-dibromo-8-azabicyclo-(3,2,1)-oct-6-en-3-one prepared by the method as described in Example 3 or 4 was dissolved in 10 ml of ethyl acetate and then subjected to hydrogenation after added thereto 40 mg of 10% Pd/C. After lapsed 20hrs., the resulting reaction mixture was filtered with use of a column filled with $NaHCO_3$, $Na_2SO_4$ and celite to remove the catalyst. The filtrate was concentrated to obtain 230 mg of a crystal substance. The substance was recrystallized from a benzene/hexane mixture to obtain 188 mg of the desired compound as white crystals (yield 91%). m.p. 149° to 150° C.

IR spectrum ($CHCl_3$) $cm^{-1}$:
1750 (C=C), 1706
Mass spectrum (m/e):
343, 341, 339 ($M^+$)

REFERENCIAL EXAMPLE 5

Preparation of N-carbomethoxy-dehydronortropinone [N-carbomethoxy-8-azabicyclo(3,2,1)oct-6-en-3-one]

A. 100 mg (0.29 mmol) of N-carbomethoxy-2,4-dibromo-8-azabicyclo(3,2,1)oct-6-en-3-one prepared by the method as described in Example 3 or 4 was dissolved in 5.0ml of methyl alcohol, 250mg of Zn—Cu couple and 200 mg of $NH_4Cl$ were added and then the resulting mixture was stirred for 20 hrs. at room temperature. After filtered off precipitate formed during the reaction, methyl alcohol and distilled out from the filtrate under a reduced pressure and then ethyl acetate was added. The resulting mixture was filtered to remove forming an insoluble substances and the filtrate was concentrated to obtain about 200 mg of an oily substance. The oily substance was subjected to a column chromatography ($SiO_2$ 3g, ethyl acetate/n-hexane = 1 : 3 to 1 : 1) to obtain 51 mg (yield 95%) of the desired substance in crystal form. Recrystallization of the substaance from 1 : 1 : 5 mixture of benzene/ethyl acetate/n-hexane at −20°C gave a white crystal which melts at 69° to 70° C.

IR spectrum ($CHCl_3$) $cm^{-1}$:
3005 (vinyl, H)
1701 (C=O and $COOCH_3$)
1000 (C=C)
Mass spectrum (m/e):
181 ($M^+$), 138 ($M^+$ − 43)

B. Under a nitrogen atmosphere, 200 mg (0.58 mmol) of N-carbomethoxy-2,4-dibromo-8-azabocyclo(3,2,1)oct-6-en-3-one prepared by the method described in Example 3 or 4, 300 mg of Zn—Cu couple and 10.1 ml of 95% aqueous solution of N, N-dimethylformamide were charged in a reaction vessel and the mixture was stirred for 5 hrs. at room temperature. Thereafter, water was added to the reaction mixture which was then extracted three times with 1 : 2 mixture of ethyl acetate/n-hexane, and the resulting extracted and combined organic layer was dried by $Na_2SO_4$ and concentrated to obtain about 200 mg of an oily substance. The oily substance had contain dimethylformamide and thus was dissolved again in 1 : 2 mixture of ethyl acetate/n-hexane, washed with water 1 time, dried and concentrated to obtain 110 mg of an oily substance. The resulting substance was subjected to a column chromatography with use of 3g of silica gel to obtain 60 mg of the desired compound in crystal form (yield 57%).

C. 5 mg of N-carbomethoxy-2,4-dibromo-8-azabicyclo(3,2,1)-oct-6-en-3-one prepared by the method as described in Example 3 or 4 and 15 mg of Zn-Cu couple were thermally treated for 1 hr. at 80° C in 0.5 ml of aqueous solution of dioxane (95%) and the reaction mixture was subjected to a thin layer chromatography to confirm facts that the starting materials have been exhausted and that only a spot which coincides with the desired compound presents.

REFERENCIAL EXAMPLE 6

Preparation of N-acetyl-2,4-dimethylnortropanol [N-acetyl-2,4-dimethyl-8-azabicyclo(3,2,1)octan-3-ol]

A. In a 10 ml reaction vessel, a rotor for magnetic stirring and 5.5 mg (1.1 equivalent) of $LiAlH_4$ were placed in and a three-way cock was mounted on the vessel. To one of three branches of the cock, a balloon filled with nitrogen gas was attached, the remaining branch was connected to a vacuum pump. After removed air in the vessel by actuating the pump, nitrogen was introduced in the vessel.

2 ml of tetrahydrofran and then a mixture of 100 mg of N-acetyl-2,4-dimethyl-8-azabicyclo(3,2,1)octan-3-one prepared by the method as described in Referencial Example 1 and 2 ml of tetrahydrofuran were charged injectionally into the reaction vessel.

After stirred the reaction mixture for 1 hr. at 0° C, the reaction mixture was checked by a thin layer chromatography (alumina, ethyl ether/n-hexane = 1 : 1, 2 times) to find unreacted raw material, and thus the mixture was further stirred for three hours at room temperature. Thereafter, the mixture was checked again by an alumina thin layer chromatography (ethyl ether/n-hexane = 1 : 1, 2 times) to find a new spot below that showing the raw material. The reaction mixture was further stirred over a night at room temperature and checked, but no change in spot could be observed.

To the reaction mixture, an excess amount of 1N-HCl was added at 0° C and the resulting mixture was stirred for 20 min. at room temperature, and extracted with use of $CHCl_3$ in 5 times. The combined extract was dried by sodium sulfate anhydride and concentrated at a reduced pressure to obtain 100 mg of an yellowish oily substance. According to a thin layer chromatography, it had been confirmed that the oily substance is a mixture with two components and thus the substance was subjected to a preparative thin layer chromatography (alumina, ethyl ether/benzene = 1 : 1, 2 times) to separate the components each other and refine the same. The refined substances were subjected to IR and NMR spectrums to confirm such facts that a part larger in Rf value is the raw material and another part with smaller Rf value is the desired substance. This had been identified based on such a fact that, according to $D_2O$ exchange, $\delta$ 3.3 − 2.8 (m, 1H) of NMR spectrum ($CCl_4$) disappears.

B. A 10 ml reaction vessel in which a rotor for magnetic stirring and 10.1 mg of $LiAlH_4$ were placed and charged was made nitrogen atmosphere and then cooled at 0° C. In the vessel, 1 ml of tetrahydrofuran and 72.3µl (1.0 equivalent) of t-butyl alcohol were added and then the mixture was stirred for 20 min. and then after added a mixture of 50 mg of N-acetyl-2,4-dimethyl-8-azabicyclo(3,2,1)octan-3-one prepared by the method as described in Referencial Example 1 and 1 ml of tetrahydrofuran, the temperature of the resulting reaction mixture was raised up gradually to room temperature and stirred for 12 hrs.

Thereafter, an excess amount of 1N-HCl was added to the reaction mixture at 0° C and then the resulting mixture was subjected to $CHCl_3$ extraction (5 times). The combined extracts were dried of sodium sulfate anhydride and concentrated under a reduced pressure to obtain 50 mg of an yellowish oily substance.

The oily substance was checked by a thin layer chromatography to find that the substance is about 1 : 1 mixture of the raw and the desired materials, which is similar to that obtained in preceding Item A.

REFERENCIAL EXAMPLE 7

Preparation of 2,4-dimethyl-6,7-dehydrotropanol [N-methyl-2,4-dimethyl-8-azabicyclo(3,2,1)oct-6-en-3-ol]

To a 30 ml reaction vessel in which a rotor for magnetic stirring and 80 mg of $LiAlH_4$ were placed and charged, a dimroth tube and then a three-way cock were mounted, one of three branches of said cock being provided with a balloon filled with nitrogen gas and the remaining branch connected to a vacuum pump, respectively. The reaction vessel was made nitrogen atmosphere. After cooled at 0° C, 10 ml of dried ethyl ether and then 130 mg (0.625 mmol) of N-carbomethoxy-2,4-dimethyl-8-azabicyclo(3,2,1)oct-6-en-3-one prepared by the method as described in Example 2 and dissolved in 10 ml of ethyl ether were injectionally charged into the vessel.

After stirred for 1 hr. at 0° C, the reaction mixture was checked by a thin layer chromatography (alumina, ethyl ether/benzene = 1 : 1) to confirm that the raw material has been exhausted and 6 spots present. The reaction mixture was then subjected to reflux for 4 hrs. and checked by a similar chromatography to find 5 spots.

After added 10 ml of distilled water and stirred for 1 hr. at 0° C, a white precipitate formed was filtered off with use of a celite and the resulting filtrate was subjected to extraction (5 times) with use of $CHCl_3$. The combined extracts were dried on sodium sulfate anhydride and concentrated under a reduced pressure to obtain 110 mg of an oily substance.

The oily substance was separated and refined by a preparative thin layer chromatography (alumina, ethyl ether/benzene = 1 : 1) to obtain following 4 kinds of alcohols and a small amount of a substance of which structure could not be confirmed.

The structures of the alcohols have been decided through various spectrum analysis and checking of $D_2O$ exchange. Rf values became larger in the following order and the alcohols have been obtained in a ratio of 1 : 8 : 6 : 3.

cis-2,4-dimethyl-6,7-dehydro-3β-tropanol,
cis-2,4-dimethyl-6,7-dehydro-3α-tropanol,
trans-2,4-dimethyl-6,7-dehydro-3β-tropanol, and
trans-2,4-dimethyl-6,7-dehydro-3α-tropanol.
cis-2,4-dimethyl-6,7-dehydro-3β-tropanol
Mass spectrum (m/e):
167 ($M^+$), 124 (M − 43), 109, 107
cis-2,4-dimethyl-6,7-dehydro-3α-tropanol
IR spectrum ($CCl_4$) $cm^{-1}$:
2970, 2940, 1170, 1072, 1045, 710
Mass spectrum (m/e):
167 ($M^-$), 134 (M = 33), 109, 108
trans-2,4-dimethyl-6,7-dehydro-3β-tropanol
IR spectrum ($CCl_4$) $cm^{-1}$:
2975, 2940, 1455, 1048, 710
Mass spectrum (m/e):
167 ($M^+$), 124 (M − 43), 109, 108
trans-2,4-dimethyl-6,7-dehydro-3α-tropanol
IR spectrum ($CCl_4$) $cm^{-1}$:
2980, 2935, 1453, 1082, 1037, 710
Mass spectrum (m/e):
167 ($M^+$), 134 (M − 33), 109, 108

REFERENCIAL EXAMPLE 8

Preparation of 2,4-dimethyltropanol
[N-methyl-2,4-dimethyl-8-azabicyclo(3,2,1)octan-3-ol]

To a 30 ml reaction vessel, a rotor for magnetic stirring and 80 mg of $LiAlH_4$ were placed in, a dimroth tube and a three-way cock were mounted, and then the inside space of the reaction vessel was made under a nitrogen atmosphere. After cooled the vessel at 0° C, 10 ml of dried ethyl ether and 124 mg of N-carbomethoxy-2,4-dimethyl-8-azabicyclo(3,2,1)octan-3-one prepared by the method as described in Referencial Example 2 and dissolved in 10 ml of ethyl ether were injectionally charged in the vessel.

After continued stirring for 1 hr. at 0° C, the reaction mixture was subjected to reflux for 12 hrs., although the reflux time might be considered as sufficient only for 3 to 4 hrs.

Thereafter, 10 ml of distilled water was added to the reaction mixture which was then stirred for 1 hr. at 0° C. The resulting mixture was filtered with use of celite to remove forming precipitate, extracted in 5 times with use of $CHCl_3$ and then the combined extract was dried by sodium sulfate anhydride and concentrated under a reduced pressure to obtain 125g of an oily substance. The oily substance was checked with use of a thin layer chromatography (alumina, ethyl ether/benzene = 1 : 1) to find 6 spots and to confirm a fact that there is remained no raw material. According to NMR spectrum analysis, it had been confirmed that —N—COOCH$_3$ radical is not present and —N—CH$_3$ radical presents to find a fact that the oily substance is a mixture of three isomers but only the following alcohol could be isolated therefrom with use of a preparative thin layer chlomatography.

cis-2,4-dimethyl-3α-tropanol

IR spectrum ($CCl_4$) $cm^{-1}$:
2970, 2940, 1450, 1055
Mass spectrum (m/e):
169 ($M^+$), 152 (M−17), 119, 117

REFERENCIAL EXAMPLE 9

Preparation of N-carbomethoxy-2,4-dibromo-6,7-dehydronortropanol [N-carbomethoxy-2,4-dibromo-8-azabicyclo(3,2,1) oct-6-en-3-ol]

To a 30 ml reaction vessel, a rotor for magnetic stirring and 75 mg of $NaBH_4$ were placed in and then the inside space of the vessel was made under a nitrogen atmosphere. In the vessel, 10 ml of distilled ethyl alcohol and 200 mg of N-carbomethoxy-2,4-dibromo-8-azabicyclo(3,2,1)oct-6-en-3-one prepared by the method as described in Example 3 or 4 and dissolved in 5 ml of ethyl alcohol were injectionally charged and then the mixture was stirred for 16 hrs. at room temperature.

After added 20 ml of aqueous solution of $NH_4Cl$, the resulting reaction mixture was extracted in 4 times with use of ethyl acetate and then the combined extract was dried on sodium sulfate anhydride and concentrated under a reduced pressure to obtain 180 mg of an oily substance.

The oily substance was checked with use of a thin layer chromatography (silica gel, ethyl ether/n-hexane = 1 : 1) to find 3 main spots.

The presence of —$NCOOCH_3$ radical was confirmed by IR spectrum analysis. The oily substance was subjected to a preparative thin layer chromatography (silica gel, ethyl acetate/n-hexane = 2 : 1) to isolate a part showing maximum Rf value and then subjected the part to NMR spectrum analysis to obtain following data and to confirm a fact that the part is the desired compound.

cis-N-carbomethoxy-2,4-dibromo-6,7-dehydronortropanol

NMR spectrum ($CDCl_3$) δ:
6.50 (t, 2H, $H_6$, $H_7$, J = 1.0Hz)
4.9 − 4.5 (m, 2H, $H_1$, $H_5$)
4.43 (dd, 2H, $H_2$, $H_4$, J = 3.0, 4.5 Hz)
4.3 − 3.7 (, 1H, $H_3$, t, J = 4.5 Hz)
3.80 (s, 3H, $NCOOCH_3$)
2.8 − 1.8 (m, 1H, —OH)

EXAMPLE 10

Preparation of tropine
[N-methyl-8-oxabicyclo(3,2,1)-octan-3α-ol]

25 mg (0.14 mmol) of N-carbomethoxy-8-azabicyclo(3,2,1)-octan-3-one prepared by the method as described in Referencial Example 3 was dissolved in 0.5 ml of benzene and then 0.6 ml of pentane solution of diisobutylaluminumhydride (1 ml/1 mmol) was added to the mixture at room temperature and the resulting mixture was stirred at room temperature.

After 12 hrs., about 2 ml of a moisture contained ethyl ether was added to said mixture and then left to stand for 30 min. at room temperature. After added ethyl acetate, the reaction mixture was filtered to remove non-soluble substances. The resulting filtrate was dried by $Na_2SO_4$ and ethyl acetate therein was distilled out under a reduced pressure to obtain 17 mg of a colorless oily substance.

The oily substance was subjected to a gas chromatography (OV1 3%, 2 m., 90° C) to confirm a fact that 2 peaks with a ratio of about 85 : 15 present (retention times were of 8.0 min. and 10.3 min., respectively). The compound having retention time of 8.0 min. was the objective substance of tropine and the other compound having retention time of 10.3 min. pseudo-tropine [N-methyl-8-oxabicyclo(3,2,1)octan-3β-ol].

Tropine formed, of which IR, NMR and Mass spectrum data were completely coincide with those of natural one was obtained in crystal form (yield 6 mg, 31%) by refining said oily substance with use of a column chromatography (alumina prepared by Merck and Co., Inc., activity II to III), but pseudotropine could not be isolated.

EXAMPLE 11

Preparation of a mixture of tropine
[N-methyl-8-oxabicyclo(3,2,1)octan-3α-ol]and
pseudo-tropine
[N-methyl-8-oxabicyclo(3,2,1)octan-3β-ol]

2.5 mg of N-carbomethoxy-8-azabicyclo(3,2,1)octan-3-one prepared by the method as described in Referencial Example 3 was dissolved in 0.1 ml of benzene, and then 0.1 ml of pentane solution of diisobutylaluminumhydride (1 ml/l mmol) was added to the mixture to heat at 50° C. After 2 hrs., a moisture contained ethyl ether was added to the resulting reaction mixture and the mixture was left to stand for 30 min.. Then the mixture was extracted in several times with use of ethyl acetate and the combined extract was concentrated to obtain a colorless oily substance.

According to a gas chromatography, the oily substance was identified as 97 : 3 mixture of tropine and pseudo-tropine.

EXAMPLE 12

Preparation of a mixture of tropine
[N-methyl-8-azabicyclo(3,2,1)octan-3α-ol]and
pseudo-tropine[N-methyl-8-azabicyclo(3,2,1)octan-3β-ol]

Under nitrogen atmosphere, 11.4 mg of LiAlH$_4$, 0.15 ml of tetrahydrofran and then 85 μl of t-butylalcohol were placed in a reaction vessel. After standing the resulting mixture for 15 min. at room temperature, a tetrahydrofran solution of N-carbomethoxy-8-azabicyclo(3,2,1)octan-3-one prepared by the method as described in Referencial Example 3 (0.1 ml/2 mg) was added to the mixture and then continued stirring for 17.5 hrs.. To the reaction mixture, a moisture contained ethyl ether was added to stop the reaction and then the reaction mixture was subjected to extraction in several times with use of ethyl acetate. The combined extract was dried with use of Na$_2$SO$_4$ and concentrated to obtain N-carbomethoxy-8-azabicyclo(3,2,-1)octan-3-ol, in crystal form.

IR spectrum (CHCl$_3$) cm$^{-1}$:
3400 (OH), 1675 (COOCH$_3$)
Mass spectrum (m/e):
185 (M$^+$)

A tetrahydrofran solution of the resulting N-carbomethoxy-8-azabicyclo(3,2,1)octan-3-ol (0.2 ml/4 mg) was added to a tetrahydrofran solution of LiAlH$_4$ (0.15 ml/9 mg) and then the mixture was stirred at room temperature under nitrogen atmosphere.

After 4 hrs., a moisture contained ethyl ether was added to the reaction mixture to left to stand for 30 min. at room temperature. The mixture was then extracted with use of ethyl acetate and checked by a gas chromatography to confirm that the product was of about 8 : 2 mixture of tropine and pseudotropine.

EXAMPLE 13

Preparation of dehydrotropine
[N-methyl-8-azabicyclo(3,2,1)oct-6-en-3a-al]

100 mg (0.29 mmol) of N-carbomethoxy-2,4dibromo-8azabicyclo(3,2,1)oct-6-en-3-one prepared by the method as described in Example 3 or 4 was dissolved in 10 ml of dimethoxyethane and 0.4 molar dimethoxyethane solution of Zn(BH$_4$)$_2$ (1.15 ml; 0.49 mmol) was added to the mixture, and then the resulting mixture was stirred for 17 hrs. at room temperature. Thereafter, about 1 ml of 0.1N—HCl was added, the reaction mixture was concentrated under a reduced pressure, extracted 4 times with use of ethyl acetate, and then the combined extract was dried and concentrated to obtain 120 mg of an oily substance with crystals. The substance was separated and refined by a silica gel column chromatography to obtain, in the first place, 25 mg of crystals and then 70 mg of white crystals. Both crystalline substances were subjected to a thin layer chromatography and NMR spectrum analysis to find that the former is adduct (raw material) and the latter N-carbomethoxy-2,4-dibromo-8-azabicyclo(3,2,-1)oct-6-en-3-ol. The alcohol was recrystallized from a mixture of benzene and n-hexane to obtain pure substance (yield: 57 mg — 57%)

N-carbomethoxy-2,4-dibromo-8-azabicyclo(3,2,1)
oct-6-en-3-ol

IR spectrum (CHCl$_3$) cm$^{-1}$:
3590 (OH), 1707 (COOCH$_3$), 1600 (C = C)
NMR spectrum (CDCl$_3$) δ:
1.8 – 2.8 (brs. 1H, OH)
3.80 (s, 3H, OCH$_3$)
3.7 – 4.3 (t, 1H, J = 4.5 Hz)
4.43 (dd, 2H, J = 3.0, 4.5 Hz, H$_2$, H$_4$)
4.5 – 4.9 (m, 2H, H$_1$, H$_5$)
6.50 (t, 2H, J = 1.0 Hz, H$_6$, H$_7$)
Mass spectrum (m/e):
343, 341, 339 (M$^+$)

Under nitrogen atmosphere, a mixture of 50 mg of LiAlH$_4$ and 4.0 ml of dimethoxyethane was cooled at −20° C, and then, to the mixture, a dimethoxyethane solution of N-carbomethoxy-2,4-dibromo-8-azabicyclo(3,2,1)oct-6-en-3-ol (1 ml/100 mg − 0.30 mmol-) was injectionally charged and the resulting mixture was stirred for 2 hrs. at −20° C, 1.5 hrs. at 0° C and 3 hrs. at room temperature, respectively.

Thereafter, the mixture was cooled again at 0° C, 0.05 ml of water was added thereto and the mixture was then stirred for a while and diluted by adding ethyl acetate. The reaction mixture was filtered to remove precipitate formed and the filtrate was dried with use of Na$_2$SO$_4$ and concentrated under a reduced pressure to obtain 46 mg of an oily substance which emits an amine like odor or smell. The substance was subjected to a gas chromatography (OV1 3%, 90° C) to find a signal which coincides with a control dehydrotropine. No dehydropseudo-tropine was by-produced.

By a quantitative analysis for which n-C$_{11}$H$_{24}$ was used as control, it was found that the 53% (compensated) of dehydrotropine and 19% (non-compensated) of an unidentified substance produce. The NMR spectrum of this mixture has contained a signal which coincides with that of a control or sample of pure dehydrotropine.

Tropine formed had not been isolated.

EXAMPLE 14

Preparation of dehydrotropine
[N-methyl-8-azabicyclo-(3,2,1)oct-6-en-3α-ol]

Under nitrogen atmosphere, 50 mg (0.28 mmol) of N-carbomethoxy-8-azabicyclo(3,2,1)oct-6-en-3-one prepared by the method as described in Referencial Example 5 was dissolved in 1.0 ml of tetrahydrofran and then the resulting solution, after added 1.2 ml of pentane solution of diisobutylaluminumhydride (1 ml/1mmol) thereto, was stirred for 20 hrs. at room temperature.

Thereafter, about 3 ml of a moisture contained ethyl ether was added to the reaction mixture and then the mixture was left to stand for 30 min. at room temperature and extracted with use of ethyl acetate. The extract was dried with use of $Na_2SO_4$ and then concentrated to obtain about 60 mg of an oily substance. This oily substance was subjected to a thin layer chromatography to observe two spots, although Rf value of the substance could not be defined due to tailing. According to a gas chromatography, two peaks were observed at retention times of 6.0 and 8.0 min. (ratio 6 : 1). The mixture was isolated and refined by subjecting to an $Al_2O_3$ column chromatography (manufactured by Merck And Co., Inc.; Activity II to III; ethyl acetate) to obtain 2.8 mg (yield 72%) of the objective dehydrotropine as oily substance.

In addition to the desired compound, about 6 mg of another substance which had been thought as dehydropseudo-tropine [N-methyl-8-azabicyclo(3,2,1)oct-6-en-3β-ol] was also isolated but, according to a gas chromatography, it has been found that the substance contains about 20% of dehydrotropine.

Dehydrotropine

IR spectrum ($CHCl_3$) $cm^{-1}$:
3600 (OH), 3055 (vinyl, H)
Mass spectrum (m/e):
139 ($M^+$), 122 ($M^+-17$)

We claim:
1. A process for the preparation N-acyldehydronortropinone having the formula:

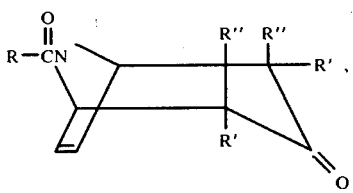

, wherein R represents a member selected from the group consisting of hydrogen, lower alkyl, lower alkoxy, phenyl and phenoxy, and R' and R" each represents the same or different member selected from the group consisting of hydrogen lower alkyl, and halogen, comprising reacting an N-acylpyrrole having the formula:

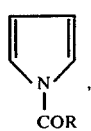

, wherein R has the meaning given above, with an α, α'-halogenoketone having the formula:

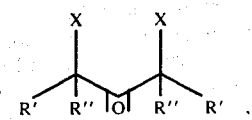

, wherein R' and R" respectively have the meanings given to them above and X represents halogen, in the presence of a reducing agent selected from the group consisting of iron carbonyl and zinc-copper couple.

2. A process as claimed in claim 1, wherein the N-acylpyrrole is reacted with the α, α'-halogenoketone in a solvent selected from the group consisting of benzene and dimethoxyethane.

3. A process as claimed in claim 2, wherein the N-acylpyrrole is reacted with the α, α'-halogenoketone in benzene at room temperature under radiation of light beam and in the presence of ironcarbonyl.

4. A process as claimed in claim 2, wherein the N-acylpyrrole is reacted with the α, α'-halogenoketone in benzene at a temperature of about 50° C in the presence of ironcarbonyl.

5. A process as claimed in claim 2, wherein the N-acylpyrrole is reacted with the α, α'-halogenoketone in dimethoxyethane at −5° C to room temperature in the presence of zinc-copper couple.

6. A process for the preparation of a hydroxy compound having a formula selected from the group consisting of:

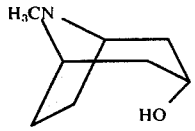

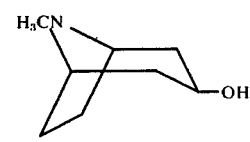

, which comprises reacting N-carbomethoxypyrrole with a tetrahaloacetone, in the presence of a reducing agent selected couple, subjecting the resulting N-carbomethoxy-2,4-dihalogeno-8-azabicyclo (3,2,1) oct-6-en-3-one to catalytic hydrogenation, reducing the resulting N-carbomethoxy-8-azabicyclo (3,2,1) octan-3-one, and recovering said hydroxy compound.

7. A process as claimed in claim 6, wherein the catalytic hydrogenation is carried out at room temperature in the presence of a solvent.

8. A process as claimed in claim 6, wherein N-carbomethoxy-8-azabicyclo (3,2,1) octan-3-one is reacted with an alkylaluminumhydride in the presence of a solvent.

9. A process as claimed in claim 8, wherein N-carbomethoxy-8-azabicyclo (3,2,1) octan-3-one is reacted with diisobutyl-aluminumhydride in benzene and at room temperature, to produce tropine.

10. A process as claimed in claim 8, wherein N-carbomethoxy-8-azabicyclo (3,2,1) octan-3-one is reacted with diisobutylaluminumhydride in benzene and at a temperature of about 50° C.

11. A process as claimed in claim 6, wherein N-carbomethoxy-8-azabicyclo (3,2,1) octan-3-one is reacted with lithiumaluminumhydride in a solvent mixture of tetrahydrofuran and tert-butyl alcohol and then resulting N-carbomethoxy-8-azabicyclo (3,2,1) octan-3-ol is further reacted with lithiumaluminumhydride in tetrahydrofuran and at room temperature.

12. A process for the preparation of a hydroxy compound having a formula selected from the group consisting of:

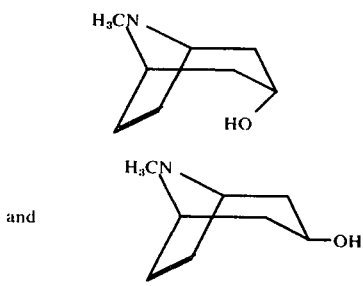

and

, which comprises reacting N-carbomethoxypyrrole with a tetrahaloacetone, in the presence of a reducing agent selected from the group consisting of iron carbonyl and zinc-copper couple, partially reducing the resulting N-carbomethoxy-2,4-dihalogeno-8-azabicyclo (3,2,1) oct-6-en-3-one, further reducing the resulting N-carbomethoxy-2, 4-dihalogeno-8-azabicyclo (3,2,1) oct-6-en-3-ol, and recovering said hydroxy compound.

13. A process as claimed in claim 12, wherein the first reduction is carried out at room temperature in the presence of Zn(BH$_4$)$_2$, and the second reduction at a temperature ranging from $-20°$ C to $0°$ C in the presence of lithiumaluminumhydride.

14. A process for the preparation of a hydroxy compound having a formula selected from the group consisting of:

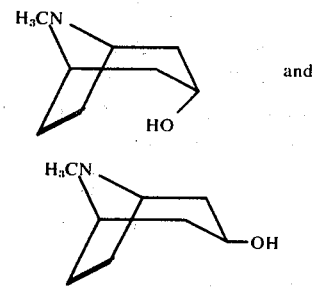

and

, which comprises reacting N-carbomethoxypyrrole with a tetrahaloacetone, in the presence of a reducing agent selected from the group consisting of iron carbonyl and zinc-copper couple, partially reducing the resulting N-carbomethoxy-2, 4-dihalogeno-8-azabicyclo (3,2,1) oct-6-en-3-one, further reducing the resulting N-carbomethoxy-8-azabicyclo (3,2,1) oct-6-en-3-one and recovering said hydroxy compound.

15. A process as claimed in claim 14, wherein the partial reduction is carried out at room temperature in methyl alcohol and in the presence of zinc-copper couple.

16. A process as claimed in claim 14, wherein the partial reduction is carried out at a temperature of about 80° C in dioxane and in the presence of zinc-copper couple.

17. A process as claimed in claim 14, wherein the second reduction is carried out at room temperature by subjecting N-carbomethoxy-8-azabicyclo(3,2,1) oct-6-en-3-one to the reaction with diisobutylaluminumhydride in tetrahydrofuran.

18. A process according to claim 1 wherein the alkyl substituents are selected from the group consisting of methyl and isopropyl.

19. A process according to claim 1 wherein the alkoxy substituent is isopropyl.

* * * * *